United States Patent
Feller et al.

(10) Patent No.: US 7,819,852 B2
(45) Date of Patent: Oct. 26, 2010

(54) SANITARY NAPKIN FOR CLEAN BODY BENEFIT

(75) Inventors: Bryan Keith Feller, Cincinnati, OH (US); Matthew Joseph Macura, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1633 days.

(21) Appl. No.: 10/600,774

(22) Filed: Jun. 20, 2003

(65) Prior Publication Data

US 2004/0260260 A1    Dec. 23, 2004

(51) Int. Cl.
*A61F 13/15* (2006.01)
*A61F 13/20* (2006.01)

(52) U.S. Cl. .................. 604/385.16; 604/385.03; 604/385.22

(58) Field of Classification Search .......... 604/391, 604/385.03, 385.16, 385.22
See application file for complete search history.

(56) References Cited

U.S. PATENT DOCUMENTS

| | | | |
|---|---|---|---|
| 4,342,314 A * | 8/1982 | Radel et al. ............... 604/370 |
| 4,619,649 A * | 10/1986 | Roberts ................... 604/396 |
| 4,623,340 A | 11/1986 | Luceri |
| 4,624,666 A | 11/1986 | DeRossett |
| 4,629,643 A | 12/1986 | Curro et al. |
| 4,655,759 A | 4/1987 | Romans-Hess |
| 4,773,905 A | 9/1988 | Molee |
| 4,865,596 A * | 9/1989 | Weisman et al. .......... 604/368 |
| 4,936,839 A | 6/1990 | Molee |
| 4,986,882 A * | 1/1991 | Mackey et al. ............ 162/109 |
| 5,092,860 A | 3/1992 | Pigneul |
| 5,135,521 A | 8/1992 | Luceri et al. |
| 5,197,959 A | 3/1993 | Buell |
| 5,342,334 A | 8/1994 | Thompson et al. |
| 5,399,175 A | 3/1995 | Glaug |
| 5,591,150 A | 1/1997 | Olsen et al. |
| 5,624,421 A | 4/1997 | Dabi et al. |
| 5,692,939 A * | 12/1997 | DesMarais ................ 442/373 |
| 5,795,344 A | 8/1998 | Chappell |
| 5,795,345 A | 8/1998 | Mizutani |
| 5,981,824 A | 11/1999 | Luceri |
| 6,096,017 A | 8/2000 | Osborn, III |
| 6,306,123 B1 | 10/2001 | Salerno et al. |
| 6,329,465 B1 * | 12/2001 | Takahashi et al. ......... 525/191 |
| 6,443,931 B1 | 9/2002 | Kurata |
| 6,447,494 B1 | 9/2002 | Kashiwagi |
| 6,447,496 B1 | 9/2002 | Mizutani |
| 6,461,339 B1 | 10/2002 | Sugahara |

(Continued)

FOREIGN PATENT DOCUMENTS

EP    0 426 235 A2    5/1991

(Continued)

*Primary Examiner*—Melanie J Hand
(74) *Attorney, Agent, or Firm*—Jason J. Camp; Roddy M. Bullock; David M. Weirich

(57) ABSTRACT

An absorbent article capable of reliably achieving an improved body-fitting profile. The absorbent article includes a fluid permeable facing layer having a first elastic modulus and an absorbent core joined to the facing layer, the absorbent core having a second elastic modulus, wherein at equal strain from about 1% to about 5% the first elastic modulus is greater than the second elastic modulus, and a fluid impermeable backsheet joined to the facing layer.

6 Claims, 4 Drawing Sheets

U.S. PATENT DOCUMENTS

| | | |
|---|---|---|
| 6,463,850 B1 | 10/2002 | Hagrud |
| 6,486,379 B1 | 11/2002 | Chen et al. |
| 6,503,233 B1 * | 1/2003 | Chen et al. .............. 604/385.01 |
| 6,506,961 B1 | 1/2003 | Levy |
| 6,517,525 B1 | 2/2003 | Berthou |
| 6,573,305 B1 * | 6/2003 | Thunhorst et al. ........... 521/50.5 |
| 6,689,935 B2 | 2/2004 | Chen et al. |
| 6,786,155 B2 * | 9/2004 | Bhambra ..................... 101/460 |
| 2002/0013565 A1 * | 1/2002 | Cinelli et al. ........... 604/385.03 |
| 2002/0065498 A1 * | 5/2002 | Ohashi et al. ................ 604/379 |
| 2003/0004484 A1 * | 1/2003 | Hammons et al. ....... 604/385.04 |

FOREIGN PATENT DOCUMENTS

| | | |
|---|---|---|
| EP | 0 617 602 B1 | 6/1992 |
| EP | 0 304 957 B1 | 4/1994 |
| EP | 0 366 079 B1 | 2/1997 |
| EP | 0 781 537 A1 | 7/1997 |
| EP | 0 597 273 B1 | 6/1998 |
| JP | H11-299822 | 11/1999 |
| WO | WO 93/01785 A1 | 2/1993 |
| WO | WO 94/04112 A1 | 3/1994 |
| WO | WO 95/17148 A2 | 6/1995 |
| WO | WO 98/27908 A1 | 7/1998 |
| WO | WO 00/25714 A1 | 5/2000 |

* cited by examiner

SANITARY NAPKIN FOR CLEAN BODY BENEFIT

FIELD OF INVENTION

This invention relates to absorbent articles such as catamenial devices and light incontinence products. In particular, this invention relates to catamenial devices such as sanitary napkins having improved comfort and body fit.

BACKGROUND OF THE INVENTION

Disposable absorbent products such as sanitary napkins, disposable diapers, and adult incontinence products are well known in the art. Such products typically have body-facing layers sometimes referred to as facing layers, and more commonly referred to as topsheets. Topsheets on disposable absorbent articles are fluid pervious sheets or webs; commonly nonwoven webs are utilized. Nonwoven webs provide fluid permeability, flexibility, and softness. Additionally, disposable absorbent products typically have absorbent cores for acquiring and storing fluids absorbed from the body and fluid impermeable backsheets to prevent acquired and/or stored fluids from contacting the body or clothing. Typically, the topsheet, backsheet and absorbent core, and optionally other layers disposed between, are disposed in a layered relationship and at least the topsheet and backsheet are typically joined along a peripheral edge.

Comfort and body fit are important design parameters for a commercially-successful absorbent article. Comfort and body fit, without sacrificing fluid handling performance are particularly important in catamenial devices such as sanitary napkins and pantiliners, as well as light incontinence pads. Such devices are designed to be worn by women via attachment to the crotch portion of their undergarments. Importantly, such devices should fit such that there is close, and preferably body-contacting, snug fit at least at the portion of the sanitary napkin positioned to receive body fluids.

Various means have been developed to improve the performance, comfort and body fit of disposable absorbent articles. For example, U.S. Pat. No. 5,197,959, issued Mar. 30, 1993 to Buell discloses a sanitary napkin having a flexure-resistant deformation element, the sanitary napkin having a convex upward configuration when the sanitary napkin is worn. The sanitary napkin relies upon the lateral compressive forces of the wearer's thighs in order to form or maintain a convex upward configuration when the sanitary napkin is worn. However, the sanitary napkin of Buell requires the addition of the deformation element, which adds cost and complexity to the device.

U.S. Pat. No. 6,447,494, issued Sep. 10, 2002 to Kashiwagi et al. discloses a sanitary napkin including a middle region and a lateral regions lying adjacent the middle region, the middle region being configured to have a rigidity lower than that of the lateral regions. One advantage claimed for Kashiwagi's device is improved fit due to napkin taking on an inverted U-shape when compressed from both sides. However, the operation of this device appears to be dependent upon a careful arrangement of adhesive spots and/or a longitudinally-oriented groove to facilitate the required deformation.

Other attempts at improved body fit include U.S. Pat. No. 6,447,496, issued Sep. 10, 2002 to Mizutani, which discloses an absorbent laminate with a deformation inducing means. The deformation inducing means is said to produce convex deformation of a panel member toward a skin contactable side of the laminate. However, the laminate of Mizutani requires relatively expensive elastically stretchable members.

Still another attempt at improving body fit of sanitary napkins is taught in U.S. Pat. No. 6,503,233 issued Jan. 7, 2003 to Chen et al. The article of Chen et al. is said to enhance body fit by way of a combination of downward-deflecting crease lines and an upward-deflecting shaping line are used in outer and central absorbent members, respectively, to achieve a form-fitting geometry in the crotch region. The form-fitting geometry is described as "W-shaped." However, the device of Chen et al. does not appear to provide for reliable body fit since the article is considered to successfully flex into a W-shape if only 60% of women who wear the article find that the W-shape is achieved and maintained in use.

Accordingly, there is a need for a disposable absorbent article having improved body fit that can be simply and economically manufactured.

Additionally, there is a need for a sanitary napkin capable of reliably achieving an improved body-fitting profile.

SUMMARY OF THE INVENTION

An absorbent article capable of reliably achieving an improved body-fitting profile is disclosed. The absorbent article comprises a fluid permeable facing layer having a first elastic modulus and an absorbent core joined to the facing layer, the absorbent core having a second elastic modulus, wherein at equal strain from about 1% to about 5% the first elastic modulus is greater than the second elastic modulus, and a fluid impermeable backsheet joined to the facing layer.

DETAILED DESCRIPTION OF THE INVENTION

While the benefits of the present invention can be enjoyed in virtually all feminine hygiene products designed to be worn in the panties of the wearer, such as sanitary napkins, pantiliners, and light incontinence products, the invention will be disclosed with respect to the Figures as a preferred embodiment of a sanitary napkin.

Figure 1:
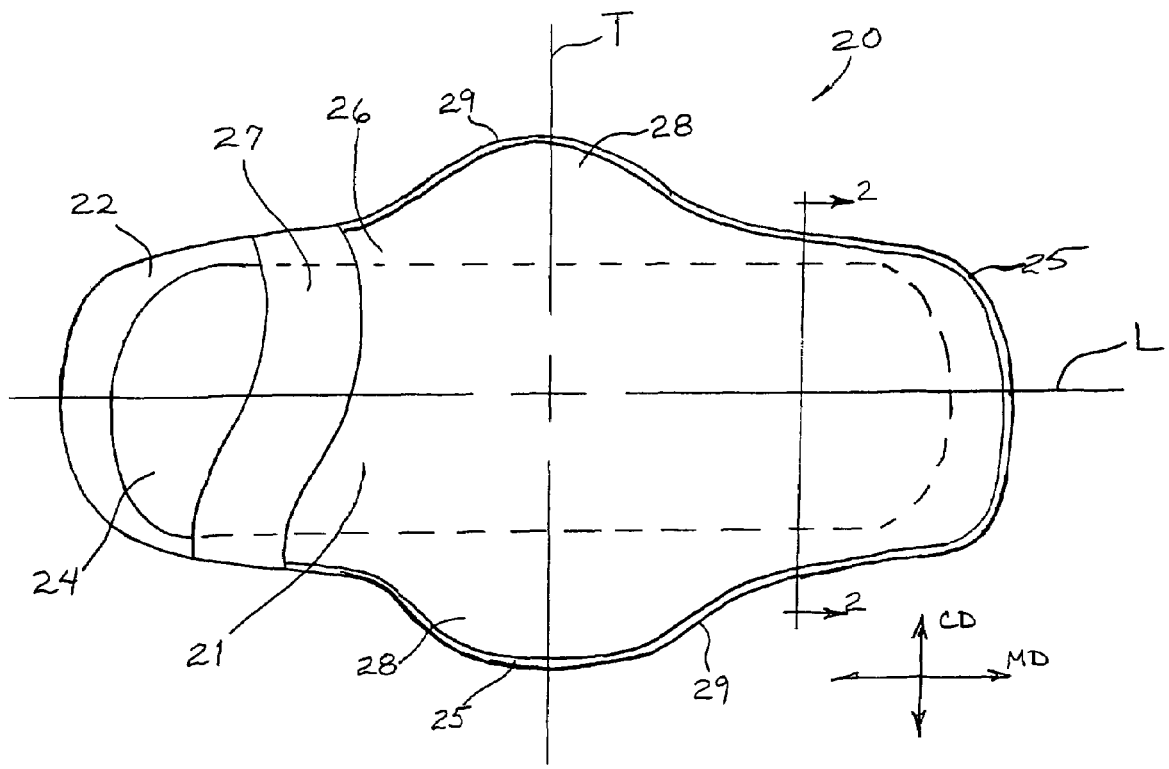
FIG. 1 is a plan view of a sanitary napkin of the present invention.

FIG. 1 shows in partial cut away plan view one embodiment of a sanitary napkin 20 of the present invention comprising a fluid permeable facing layer 21, fluid impermeable backsheet 22, and an absorbent core 24 disposed between the facing layer 21 and backsheet 22 which can be joined about a periphery 25. Facing layer 21 of sanitary napkin 20 can be a body-contacting layer commonly known in the art as a topsheet 26. Facing layer 21 can be a composite comprising a topsheet 26 and a secondary topsheet 27, as shown in FIG. 1 and also as known in the art.

Sanitary napkin 20 can have side extensions 28, commonly referred to as "wings," designed to wrap the sides of the crotch region of the panties of the user of sanitary napkin 20. Sanitary napkin 20 and/or wings 28 typically have fastening means (not shown) to releasably affix the sanitary napkin 20 to the panty. Fastening means can be pressure sensitive adhesive means or mechanical fasteners, such as hook and loop fasteners.

The sanitary napkin 20 can be made by hand or on commercial high-speed production lines as is known in the art.

The sanitary napkin 20, as well as each layer or component thereof can be described as having a "body facing" surface and a "garment facing" surface. As can be readily understood by considering the ultimate use for sanitary napkins, the body facing surfaces are the surfaces of the layers or components that are oriented closer to the body when in use, and the garment facing surfaces are the surfaces that are oriented closer to the garment of the user when in use. Therefore, for example, facing layer 21 has a body facing surface 30 (that can actually be a body contacting surface), and a garment facing surface 31 that is the surface that can be adhered to the underlying absorbent core. The garment facing surface 32 of a fluid impermeable backsheet 22 of a sanitary napkin, for example, is oriented closest to, and may contact, the wearer's panties in use (via adhesive attachment means, if used).

Figure 2:
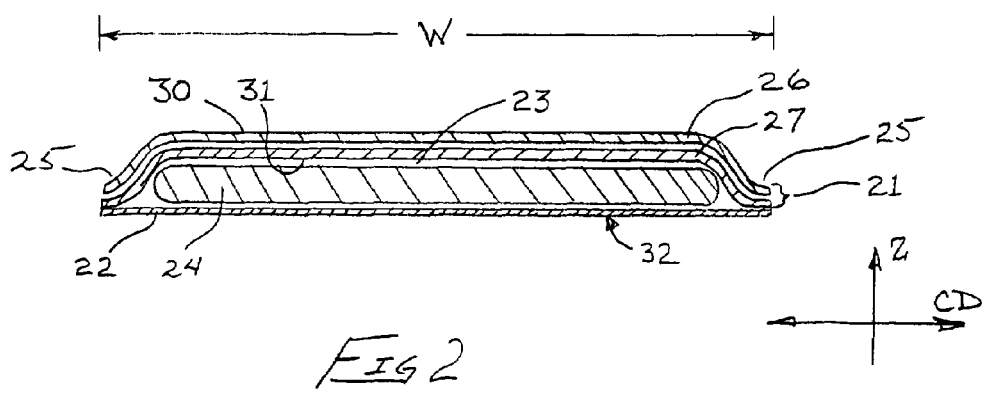
FIG. 2 is cross sectional view of Section 2-2 of FIG. 1.

Sanitary napkin 20 has a longitudinal axis L and a transverse axis T. Longitudinal axis L and transverse axis T define a two-dimensional plane of the sanitary napkin prior to use, which, in the embodiment shown is associated with the machine direction (MD) and cross machine direction (CD) as is commonly known in the art of making sanitary napkins in high-speed commercial production lines. The sanitary napkin 20 has a length, which is the longest dimension measured parallel to the longitudinal axis L. The sanitary napkin has a width, which is the dimension measured in the CD, e.g., parallel to the transverse axis. The width can vary or be substantially constant along the length of the sanitary napkin. In general, the width can be measured between lateral edges 29 parallel to the transverse axis T. However, for purposes of the present invention, a more critical dimension is important, referred to herein as the "effective width $W_e$," discussed in more detail below. The effective width $W_e$ is the width effective in facilitating portions of the sanitary napkin to be deformed "out-of-plane," i.e., buckled, or deflected upwardly, and is generally the width of absorbent core 24 measured parallel to the transverse axis, or the width between embossed channels, as disclosed more fully below. In general, by "out-of-plane" is meant extending in the "Z"-direction, as indicated by FIG. 2, and by "upward" is meant upward with respect to the orientation of FIGS. 2 and 3, which corresponds to the upward direction of a standing wearer of a sanitary napkin 20.

Facing layer 21 can comprise nonwoven materials as are known in the art for topsheets on disposable absorbent articles. Absorbent core 24 and backsheet 22 can likewise comprise absorbent materials, and film materials, respectively, as is well known in the art. Secondary topsheet 27 (if used) can be a distribution layer that serves to distribute fluid in the directions of MD and CD prior to being absorbed and stored in absorbent core 24. Wings 28, if used, can be integral extensions of the topsheet or the backsheet or both, and they can be symmetric about the longitudinal axis L, transverse axis T, or both.

Nonwoven webs used in the present invention can be any known nonwoven webs or composites of two or more nonwoven webs, each comprising fibers having sufficient mechanical (e.g., elongation) properties to be utilized as facing layer 21 as described more fully below. Fibers can be monocomponent, bicomponent, biconstituent, or capillary channel fibers.

As used herein, the term "nonwoven web" refers to a web having a structure of individual fibers or threads which are interlaid, but not in a regular, repeating manner as in a woven or knitted fabric. Nonwoven webs or fabrics have been formed from many processes, such as, for example, meltblowing processes, spunbonding processes, hydroentangling processes, and bonded carded web processes. The basis weight of nonwoven fabrics is usually expressed in grams per square meter (gsm) and the fiber diameters are usually expressed in microns. Fiber size can also be expressed in denier. The basis weight of nonwoven webs useful as components of the present invention, such as the facing layer 21 (which can be a single layer or a composite of more than one layer), can range from 10 gsm to 200 gsm.

The constituent fibers of nonwoven webs can be polymer fibers, and can be monocomponent, bicomponent, and/or biconstituent, capillary channel fibers, and can have major cross-sectional dimensions (e.g., diameter for round fibers) ranging from 5-200 microns. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "capillary channel fibers" refers to fibers having capillary channels capable of facilitating fluid movement via capillarity. Such fibers can be hollow fibers, for example, but are preferably fibers having capillary channels on their outer surfaces. The capillary channels can be of various cross-sectional shapes such as "U-shaped," "H-shaped," "C-shaped," and "V-shaped."

Sanitary napkins of the present invention provide for improved body fit, as well as improved comfort, while absorbing all or most of any fluid discharges experienced by the wearer. These advantageous properties are a result of the shape the sanitary napkin takes on during use. Although provided in a generally flat configuration, upon use portions of a sanitary napkin of the present invention deform upwardly, i.e., toward the wearer's body, such that the body-facing surface of the napkin is in close proximity, or even in contact with, the wearer's body at the point of fluid discharge, thereby enhancing both the comfort of the wearer and the performance of the sanitary napkin.

Figure 3:
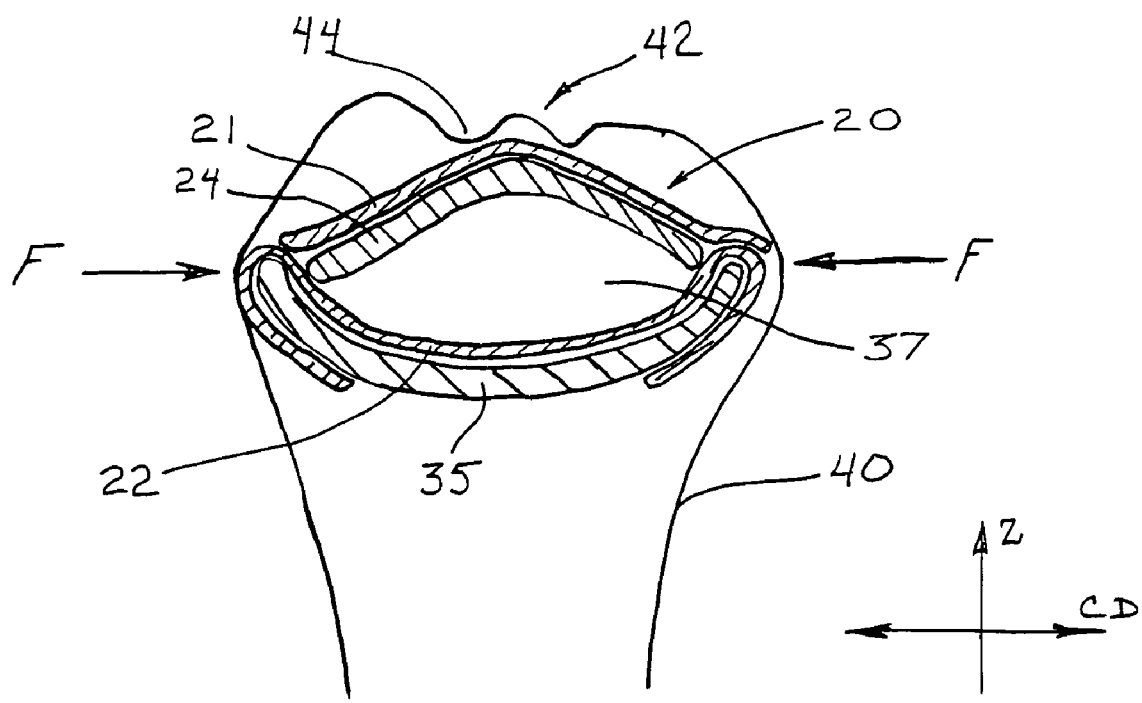
FIG. 3 is a cross sectional view of a portion of the present invention in use.

FIG. 3 is a cross-sectional view of a sanitary napkin 20 of the present invention in use, that is, being worn in the panties 35 of a wearer, indicated as 40. The sanitary napkin is placed in the crotch portion of the panty 35 and the wings 28, if any, are wrapped around the side edges of the panty and secured to the underside of the crotch portion of the panty. The cross-section shown in FIG. 3 is in the proximity of the pudendal region 42 of the wearer, and specifically in the region of the wearer's labia 44.

It has been surprisingly discovered that, when a facing layer 21 and absorbent core 24 as described and joined herein are utilized in a sanitary napkin 20, upon lateral compression due to application of a lateral compression force, designated as force F in FIG. 3, portions of the facing layer 21 and the absorbent core 24, deform, i.e., deflect, as a unit upwards (i.e., in the "up" direction with respect to a standing wearer), or, in general, towards the body of the wearer (i.e., in the "z-direction" as shown in FIGS. 2 and 3). This upward deflection or deformation places the upwardly deflected portion of the sanitary napkin into close proximity to, possibly even in contact with, the body of the wearer. As shown in FIG. 3, the central portion of the facing layer 21/absorbent core 24, i.e., the portion corresponding to a longitudinal centerline, exhibits the greatest amount of deformation, resulting in the facing layer 21/absorbent core 24 taking on the cross-sectional configuration of an inverted "V" shape. By being in close proximity to, and particularly by being in contact with, the body of the wearer, not only is performance actually enhanced, but the wearer's subjective perception of protection against leakage can be enhanced as well.

In general, as shown in FIG. 3, the backsheet 22 of the sanitary napkin 20 does not deflect upwardly, but remains positioned on the panty as placed, e.g., affixed thereto by panty fastening adhesive. This can result in a separation of the absorbent core 24 and the backsheet 22, with the amount of separation being proportional to the amount of upward deformation of the facing layer 21/absorbent core 24. The void area 37 defined between the garment-facing surface of absorbent core 24 and the backsheet 22

For a given effective width $W_e$, the amount of upward deformation of the facing layer 21 and absorbent core 24 exhibited by sanitary napkin 20 is directly proportional to the amount of strain experienced due to lateral compression. Because a sanitary napkin can have a varying effective width $W_e$, and since in use the amount of compression forces exerted laterally by the wearer's legs varies with respect to the longitudinal position along the sanitary napkin, a sanitary napkin 20 of the present invention has the beneficial quality of exhibiting varying amounts of z-direction deformation, with the greatest deformation (i.e., "highest" with respect to the upward, z-direction) being possible in the regions where the most deformation is desired. In the region corresponding to the wearer's labia, as shown in FIG. 3, for example, the lateral compression exerted by the wearer's legs is generally the greatest since the inside of the wearer's thighs produce the greatest lateral compression forces on this portion of a sanitary napkin. Therefore, the effective width $W_e$ can be made such that the upward deformation can be greatest in this portion of the sanitary napkin, resulting in the facing layer 21/absorbent core 24 being in close proximity to the body in this region. This is a beneficial improvement in sanitary napkin design, since it is precisely in the wearer's labial region that sanitary napkins generally do not come in close proximity to the wearer's body, resulting in poor body fit and increased leakage of fluid. Additionally, at the longitudinal ends of the sanitary napkin, i.e., the "front" and "back" portions of the sanitary napkin corresponding in use to the wearer's forward vulvar region and the region of the wearers gluteal groove, a sanitary napkin 20 of the present invention exhibits the least upward deformation of the facing layer/absorbent core, again, contributing to the overall performance of the sanitary napkin and the comfort of the wearer.

Figure 4:
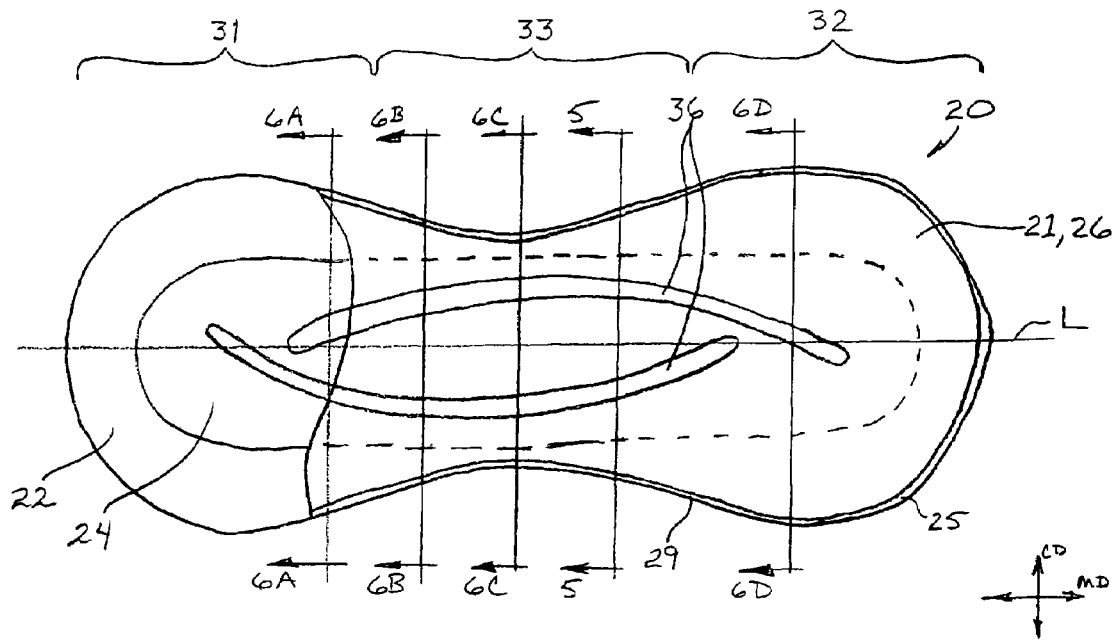
FIG. 4 is a plan view of a sanitary napkin of the present invention having channels.

To improve on both the aesthetic appearance of a sanitary napkin 20 as well as the predictability of the functionality of the facing layer 21/absorbent core 24, the sanitary napkin 20 can be provided with longitudinally-oriented embossments, referred to herein as channels 36, as shown in FIG. 4. The pair of channels 36 shown in FIG. 4 have a preferred orientation for the present invention, the pair of channels forming a shape that can be referred to as "eye-shaped" because of the general appearance of each ovolo-shaped channel as shown in FIG. 4. Eye-shaped channels can be open ended and/or offset as shown in FIG. 4, or they can be closed ended, i.e., lenticular-shaped. The sanitary napkin 20 shown in FIG. 4 does not have wings, but is generally "hour-glass" shaped, and has a pair of channels 36 embossed into the body-facing surface, specifically in the facing layer and absorbent core. The presence of channels improves the fluid handling characteristics of the sanitary napkin by preventing lateral fluid runoff of the facing layer prior to absorption into the absorbent core. Embossing facing layer 21 deep into absorbent core 24 provides for a lateral fluid run-off-impeding channel that helps contain lateral fluid flow, and, as well, adds to the aesthetic appearance of the sanitary napkin 20. It has also been surprisingly found that the presence of channels aids in the formation of upwardly-deforming portions of the sanitary napkin during use.

Figure 5:
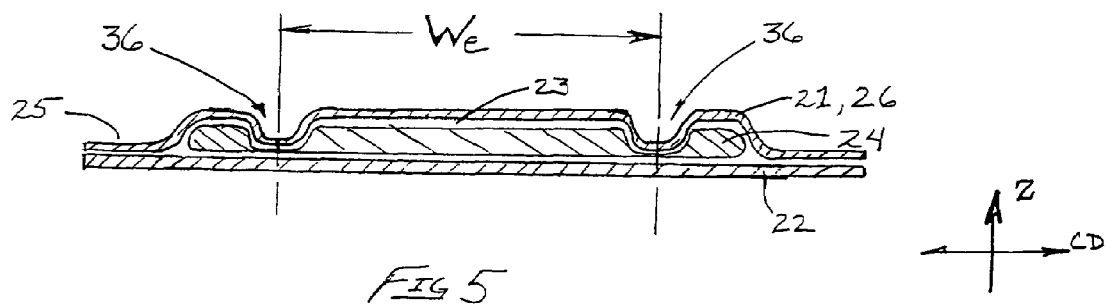
FIG. 5 is a cross sectional view of Section 5-5 of FIG. 4.

As shown in cross section in FIG. 5, which shows the sanitary napkin 20 of FIG. 4 prior to use in its generally flat two-dimensional configuration, the deep embossed channels 36 can significantly compress the absorbent core 24 in the region of channel(s) 36. By way of example, deep embossed channels 36 can have a depth dimension in the Z-direction of at least about 50% of the caliper (thickness in the Z-direction) of the sanitary napkin 20, more preferably about 60%, 70%, 80% or 90% of the caliper. Thus, if the caliper of the sanitary napkin 20 is 10 mm, the depth of embossment of channel(s) 36 measured from the body-facing surface of sanitary napkin can be 6 mm, 7 mm, 8 mm, or 9 mm. In general, the width of channels 36 can be constant, and it can be up to 100% of the depth. The width of channel 36 can be 20%, 30%, 40% or 50% or more of the depth, as well. Caliper, width and depth dimensions can be average dimensions if any are not constant across the entire sanitary napkin.

As mentioned above, it has been found that the presence of channels 36 has an effect on the way the sanitary napkin deforms during use. Specifically, the out-of-plane, upward deflection of the facing layer and absorbent core, as shown in FIG. 3, can be confined to the portion of the sanitary napkin between the channels 36. Therefore, the amount of deformation out-of-plane on various points along the longitudinal axis can be controlled to a certain extent by the shape and placement of channels. For this reason, in addition to the width W of sanitary napkin there is defined an effective width, $W_e$, which is generally the width of the sanitary napkin interiorly between the channels 36, and specifically the width between the centerlines of the channels 36, as shown in FIG. 5. In the absence of two channels having a separating dimension parallel to the transverse axis (e.g., no channels, or one channel as shown at cross-section 6D in FIG. 4), the effective width $W_e$ is considered to be the width of absorbent core 24.

Figure 6A:
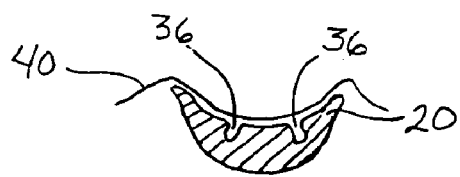
FIGS. 6A-6D are cross sectional views at the sections shown in FIG. 5 after lateral compression.

In use, therefore, the amount of upward deformation of portions of the sanitary napkin can be controlled based on the effective width $W_e$. This facilitates the design of a sanitary napkin in which the amount and location of upward deformation can be affected and enhanced based on the effective width $W_e$ that can vary along the longitudinal length of the sanitary napkin. FIG. 6A corresponds to a portion of a sanitary napkin that would be disposed in use in the frontal vulvar region of a wearer 40, and which would typically experience very little lateral compressive forces F. As can be seen in FIG. 6A, very little upward deformation of the absorbent core is exhibited where there is both low lateral compression forces and the effective width is relatively small.

Figure 6B:
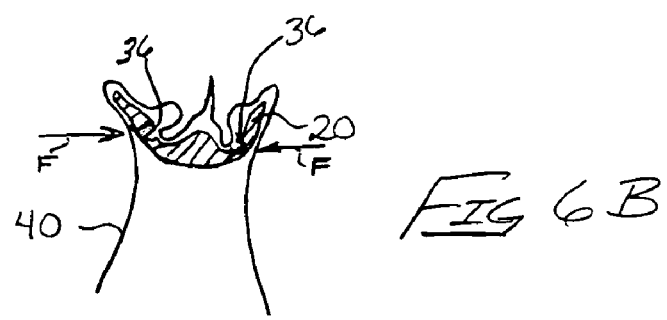
Figure 6C:
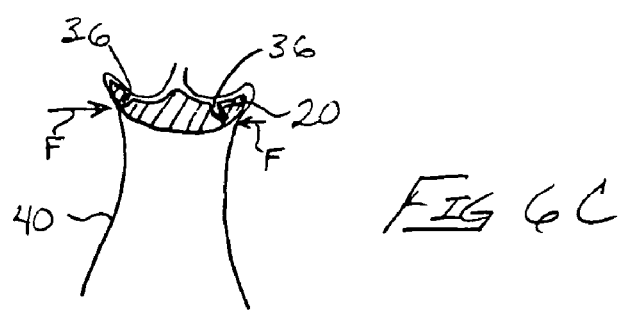

FIGS. 6B and 6C show an in-use cross-section of a sanitary napkin 20 in the labial region and the introitus region of the wearer 40, respectively. As can be seen in both FIGS. 6B and 6C, the inside of the thighs of the wearer provide a sufficient lateral compressive force F to cause an upward buckling of the facing layer 21/absorbent core 24 which results in the substantially inverted V-shaped cross-sectional configuration within the effective width at or near the portions of the pudendal region in which vaginal discharge occurs.

Figure 6D:
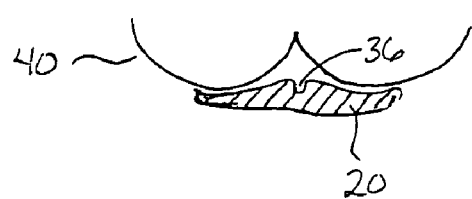

FIG. 6D shows an in-use cross-section of a sanitary napkin 20 disposed adjacent the wearer's 40 gluteal groove. As shown, very little upward deformation of the facing layer 21/absorbent core 24 is exhibited since there is little or no lateral compressive force F to cause an upward buckling of the facing layer 21/absorbent core 24.

As can be appreciated by considering FIGS. 6A-6D, the sanitary napkin 20 of the present invention provides the benefit of improved body fit by facilitating upward deflection of portions of the sanitary napkin only where such upward deflection is desired. Further, the upward deflection that is due to a buckling upwardly of the facing layer 21/absorbent core 24 occurs without the need for the user to do anything differently from what she already does in using a sanitary napkin. The user simply removes a flat, substantially two-dimensional sanitary napkin 20 from its packaging, secures it in the crotch region of her panty, and pulls the panty up and into place. The natural motion of her body, and the compression of the inside of her thighs causes the upward deformation of the facing layer 21/absorbent core 24, providing for both comfort and better fluid handling performance.

In the sanitary napkin 20 of the present invention the upward deformation of the facing layer 21/absorbent core 24, which results in improved comfort and performance, is achieved by combining facing layer 21 and absorbent core 24 materials having specified material properties in a bonded, substantially unitary design. These two components, typically de-coupled in prior art sanitary napkins, are therefore coupled in a defined relationship. Specifically, each component, i.e., the facing layer 21 and the absorbent core 24 together have a specified relationship of elastic moduli. That is, each material has an elastic modulus, and the choice of materials for each component is made based on the relative magnitude of each material's elastic modulus. In general, the sanitary napkin 20 of the present invention comprises a facing layer 21 and an absorbent core 24 wherein for equal amounts of strain the elastic modulus of the facing layer 21 is greater than the elastic modulus of the absorbent core 24 and the two components are joined at their interface 23 sufficiently so as to deform as a unitary component.

For practical purposes measuring the elastic modulus of materials, the level of strain of interest is within the elastic region, which for most materials of interest for disposable absorbent articles under about 5% strain. Therefore, in one embodiment the present invention comprises a facing layer 21 and an absorbent core 24 wherein for equal amounts of strain from about 1% to about 5% the elastic modulus of the facing layer 21 is greater than the elastic modulus of the absorbent core 24.

The elastic modulus of the facing layer 21 is preferably from about 6 kPa to about 700 kPa. The elastic modulus of the absorbent core 24 is preferably from about 0.3 kPa to about 2.0 kPa. The absorbent core 24 preferably has a density of from about 0.05 grams per cubic centimeter ($g/cm^3$) to about 0.15 grams per cubic centimeter ($g/cm^3$).

In one embodiment of the present invention the facing layer 21 comprised an apertured formed film topsheet 26 as disclosed in U.S. Pat. No. 4,629,643, obtained from Tredegar Film Products, Terre Haute, Ind. under the designation X27121 and an 80 gsm nonwoven web secondary topsheet 27 available from Concert Industries Ltd., Gatineau, Canada, under the designation MH 080.105. The topsheet 26 and secondary topsheet 27 were joined by Findley HX1500-1 meltblown adhesive applied at a loading of approximately 6.4 gsm, resulting in a facing layer having a caliper (i.e., a thickness) of about 2 mm. This facing layer has an elastic modulus of about 350 kPa. The absorbent core was Foley Fluff pulp available from Buckeye Technologies Inc., Memphis, Tenn. that was disintegrated and formed into a core having a density of about 0.07 grams per cubic centimeter ($g/cm^3$) resulting in an absorbent core having a caliper of about 10 mm. This absorbent core has an elastic modulus of about 0.5 kPa. The absorbent core was adhered to the secondary topsheet by the same Findley HX1500-1 adhesive applied in a spiral pattern at a loading of about 4.0 gsm. These components were incorporated into an absorbent article having a fluid impermeable backsheet for use as a sanitary napkin. The caliper of the component layers can be determined by any of many well-known means known in the art.

The elastic modulus is a constitutive property of materials that can be determined by any of many well-known means known in the art. In general, persons skilled in the art will recognize that any of compressive test, tensile test, or bending tests as are known and used in conjunction with testing equipment made by Instron, MTS, Thwing-Albert, and the like, can be used to measure stress/strain, particularly within the elastic region, and to report elastic modulus. It is implied herein that any of the compressive forces, tensile forces and bending forces be measured at appropriate rates of strain for in use conditions. An appropriate rate of strain is defined as anything from 100% strain in about 2 seconds to 100% strain in about 3 minutes. The ratio of the elastic modulus of the facing layer to the elastic modulus of the absorbent core can be from about 6 to 1 to about 2000 to 1, and is preferably from about 700 to 1 to about 1000 to 1.

Additionally, because the elastic modulus of materials useful for the facing layer (e.g., soft, pliable nonwovens), and absorbent core (e.g., cellulosic webs, airfelt, fluff, and the like) can have non-linear stress-strain curves over the strain range of interest, another way of stating the relationship of the material properties of the facing layer and the absorbent core is with respect to the tangent modulus of each material at a given strain level. The tangent modulus is simply the derivative of the stress-strain curve at any given strain level. Therefore, using engineering stress and engineering strain as the measured parameters, the facing layer and absorbent core of the present invention are chosen such that the tangent modulus of the facing layer is always greater than the tangent modulus of the absorbent core for any given strain within a certain range. For example, at any strain from about 1% to about 50% the tangent modulus of the facing layer is greater than the tangent modulus of the absorbent core.

For a sanitary napkin in which it is desirable to have close, snug body fit of the facing layer to the wearers pudendal region, the effective width $W_e$ must be greater than a minimum dimension in the region of the sanitary napkin intended to be worn adjacent the pudendal region of the wearer, e.g., the labia and vaginal orifice. For most sanitary napkins this region is the longitudinally central portion of the sanitary napkin, designated as 33 in FIG. 4, for example. If the sanitary napkin were to be divided along the longitudinal axis into thirds, this central portion 33 could be referred to as occupying the middle third of the sanitary napkin between a front portion 31 and a back portion 32 also as shown in FIG. 4, for example. In general, the effective width $W_e$ in the central portion 33 of the sanitary napkin must be sufficiently great such that the wearer's inner thighs can exert sufficiently high lateral forces so as to cause upward deformation of the facing layer and absorbent core. It appears that for a sanitary napkin not having channels the effective width $W_e$ in the central portion 33 should be at least about 40 mm, more preferably about 50 mm, more preferably about 60 mm, and it can be as high as 80 mm. For a sanitary napkin having a pair of channels 36, the effective width $W_e$ should be at least about 20 mm, more preferably about 30 mm, more preferably about 35 mm, and it can be as high as 50 mm.

Joining of the facing layer 21 and the absorbent core 24 can be by any means known in the art, such as by adhesive bonding, thermal bonding, ultrasonic bonding, and the like. While complete bonding at interface 23 is not necessary, it is believed that the bonding should be sufficient to facilitate the components act, as a unit, e.g., bending out-of-plane together upon sufficient lateral force, as described more fully below. In a preferred embodiment, the facing layer 21 is adhered to the body-facing side of the absorbent core 24 at substantially the entire surface interface between the two components, e.g., by the use of meltblown thermoplastic adhesive. Adhesion can be by application of a substantially uniform layer of adhesive applied by means known in the art, such as by spraying or slot coating. The adhesive, if uniformly coated should not block fluid flow into the absorbent core. Therefore, in a preferred embodiment, the adhesive is a fluid permeable adhesive, such as the aforementioned Findley HX1500-1 adhesive.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising,
   a. a fluid permeable facing layer having a first elastic modulus;
   b. an absorbent core joined to the facing layer, the absorbent core having a second elastic modulus;
   c. wherein at equal strain from about 1% to about 5% the first elastic modulus is greater than the second elastic modulus and wherein the facing layer is joined to the absorbent core at substantially the entirety of their respective interfacial surfaces;
   d. a fluid impermeable backsheet joined to the facing layer; and
   e. a pair of deep-embossed channels, the channels defining an effective width of from about 20 mm to about 50 mm.

2. The absorbent article of claim 1, wherein the density of the absorbent core is between about 0.050 g/cm$^3$ and about 0.15 g/cm$^3$.

3. The absorbent article of claim 1, wherein the facing layer has a caliper and the absorbent core has a second caliper, and wherein the ratio between the facing layer caliper and the absorbent core caliper is from about 1:3 to about 1:20.

4. The absorbent article of claim 1, wherein the absorbent article is a catamenial device.

5. The absorbent article of claim 1, wherein said topsheet is an apertured, formed film topsheet.

6. The absorbent article of claim 1, wherein said secondary topsheet is a nonwoven web.

* * * * *